(12) United States Patent
Winslow et al.

(10) Patent No.: US 8,845,744 B2
(45) Date of Patent: Sep. 30, 2014

(54) ULNAR HEAD IMPLANT

(75) Inventors: Nathan A. Winslow, Warsaw, IN (US); Thomas M. Vanasse, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 53 days.

(21) Appl. No.: 13/346,099

(22) Filed: Jan. 9, 2012

(65) Prior Publication Data
US 2013/0178944 A1 Jul. 11, 2013

(51) Int. Cl.
*A61F 2/38* (2006.01)

(52) U.S. Cl.
USPC ...................................................... 623/20.11

(58) Field of Classification Search
CPC ....................... A61F 2/4261; A61F 2002/4269
USPC ........... 623/21.11–21.18, 20.14, 20.28, 20.29
See application file for complete search history.

(56) References Cited

U.S. PATENT DOCUMENTS

| 6,656,225 | B2 * | 12/2003 | Martin | 623/20.12 |
| 7,160,329 | B2 * | 1/2007 | Cooney et al. | 623/20.11 |
| 7,658,767 | B2 * | 2/2010 | Wyss | 623/20.29 |
| 7,871,442 | B2 * | 1/2011 | Servidio | 623/20.27 |
| 8,052,755 | B2 * | 11/2011 | Naidu | 623/21.12 |
| 8,268,006 | B2 * | 9/2012 | Meyers et al. | 623/20.29 |
| 8,366,784 | B2 * | 2/2013 | Palmer | 623/21.12 |
| 8,398,717 | B2 * | 3/2013 | Kleinman | 623/21.12 |
| 2005/0049710 | A1 * | 3/2005 | O'Driscoll et al. | 623/20.11 |
| 2009/0031905 | A1 | 2/2009 | Howard | |
| 2010/0030339 | A1 * | 2/2010 | Berelsman et al. | 623/20.11 |
| 2011/0006625 | A1 | 1/2011 | Fujii et al. | |
| 2013/0116796 | A1 * | 5/2013 | Palmer | 623/21.12 |
| 2013/0218285 | A1 * | 8/2013 | Kleinman et al. | 623/21.12 |
| 2013/0297033 | A1 * | 11/2013 | Kleinman et al. | 623/21.12 |
| 2014/0074246 | A1 * | 3/2014 | Huebner et al. | 623/20.11 |

FOREIGN PATENT DOCUMENTS

FR 2660856 10/1991
WO WO 2008/026135 3/2008

OTHER PUBLICATIONS

International Search Report, mailed Feb. 11, 2013, Appln. No. PCT/US2012/068849.

* cited by examiner

*Primary Examiner* — Alvin Stewart
(74) *Attorney, Agent, or Firm* — Harness, Dickey

(57) ABSTRACT

The present teachings provide an ulnar head implant. The implant can include a head component adapted to articulate with a portion of the anatomy. The head component can define a coupling bore through a surface. The implant can also include a stem component having a base and a post that extends from the base for insertion into a prepared portion of an anatomy. The base can include a coupling feature. The implant can include an intermediate component receivable within the coupling bore and couplable to the coupling feature to couple the head component to the stem component.

13 Claims, 5 Drawing Sheets

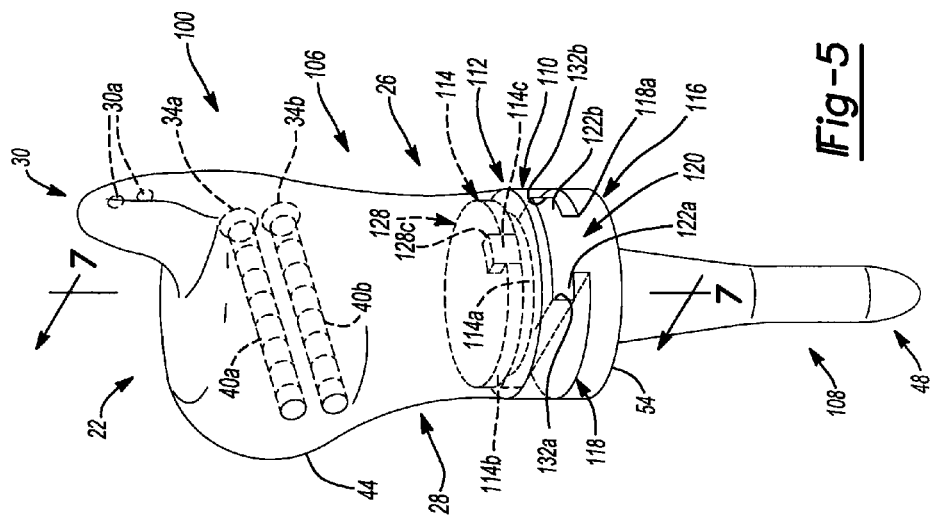
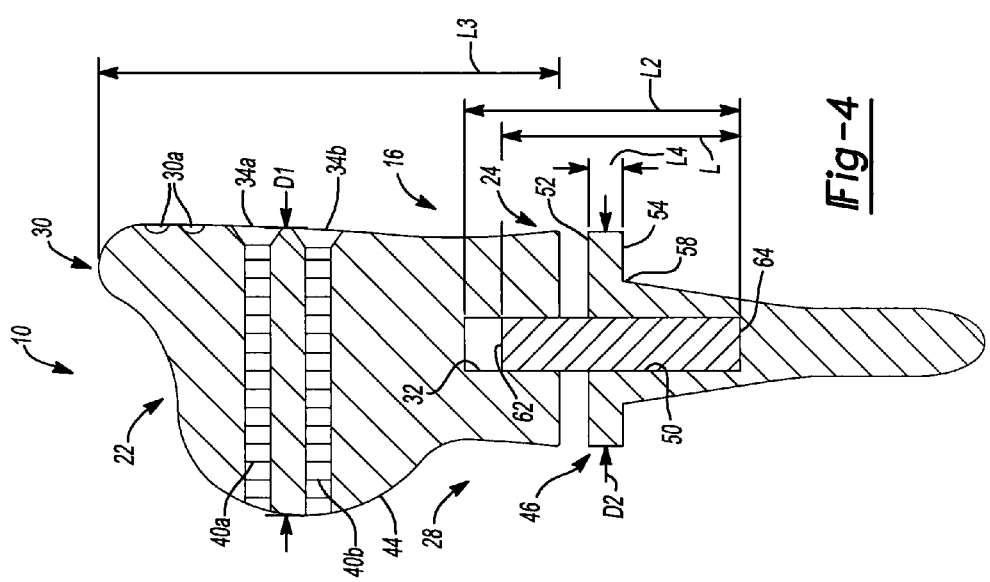

ULNAR HEAD IMPLANT

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function or repair the damaged tissue. Surgical intervention can include any surgical procedure that can restore function to the damaged tissue, which can require the use of one or more orthopedic prostheses, such as orthopedic nails, screws, implants, etc., to restore function to the damaged tissue.

The present disclosure relates to a prosthesis for use in restoring function to damaged tissue, and more specifically relates to an ulnar head implant.

SUMMARY

According to various aspects, provided is an ulnar head implant. The implant can include a head component adapted to articulate with a portion of the anatomy. The head component can define a coupling bore through a surface. The implant can also include a stem component having a base and a post that extends from the base for insertion into a prepared portion of an anatomy. The base can include a coupling feature. The implant can include an intermediate component receivable within the coupling bore and couplable to the coupling feature to couple the head component to the stem component.

Additionally provided is an ulnar head implant. The implant can comprise a head component adapted to articulate with a portion of the anatomy. The head component can define at least one bore that extends from a first side to a second, opposite side along a first axis and a counterbore that extends along a second axis transverse to the first axis. The implant can include a stem component having a base and a post that extends from the base for insertion into a prepared portion of an anatomy. The implant can also include an intermediate component receivable within the counterbore of the head component to enable the head component to move relative to the stem component about at least two degrees of freedom.

Further provided is a method of using an ulnar head implant. The method can include coupling a stem component to a first portion of an anatomy, and coupling an intermediate component to a head component. The method can also include coupling the intermediate component to the stem component so that that the head component is movable relative to the stem component about at least one degree of freedom. The method can include inserting at least one fastener through a bore defined in the head component to secure the head component to a second, different portion of the anatomy.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 4 is a cross-sectional view of the ulnar head implant of FIG. 1, taken along line 4-4 of FIG. 2;

FIG. 5 is a perspective view of another exemplary ulnar head implant according to the present teachings;

DESCRIPTION OF VARIOUS ASPECTS

Figure 1:
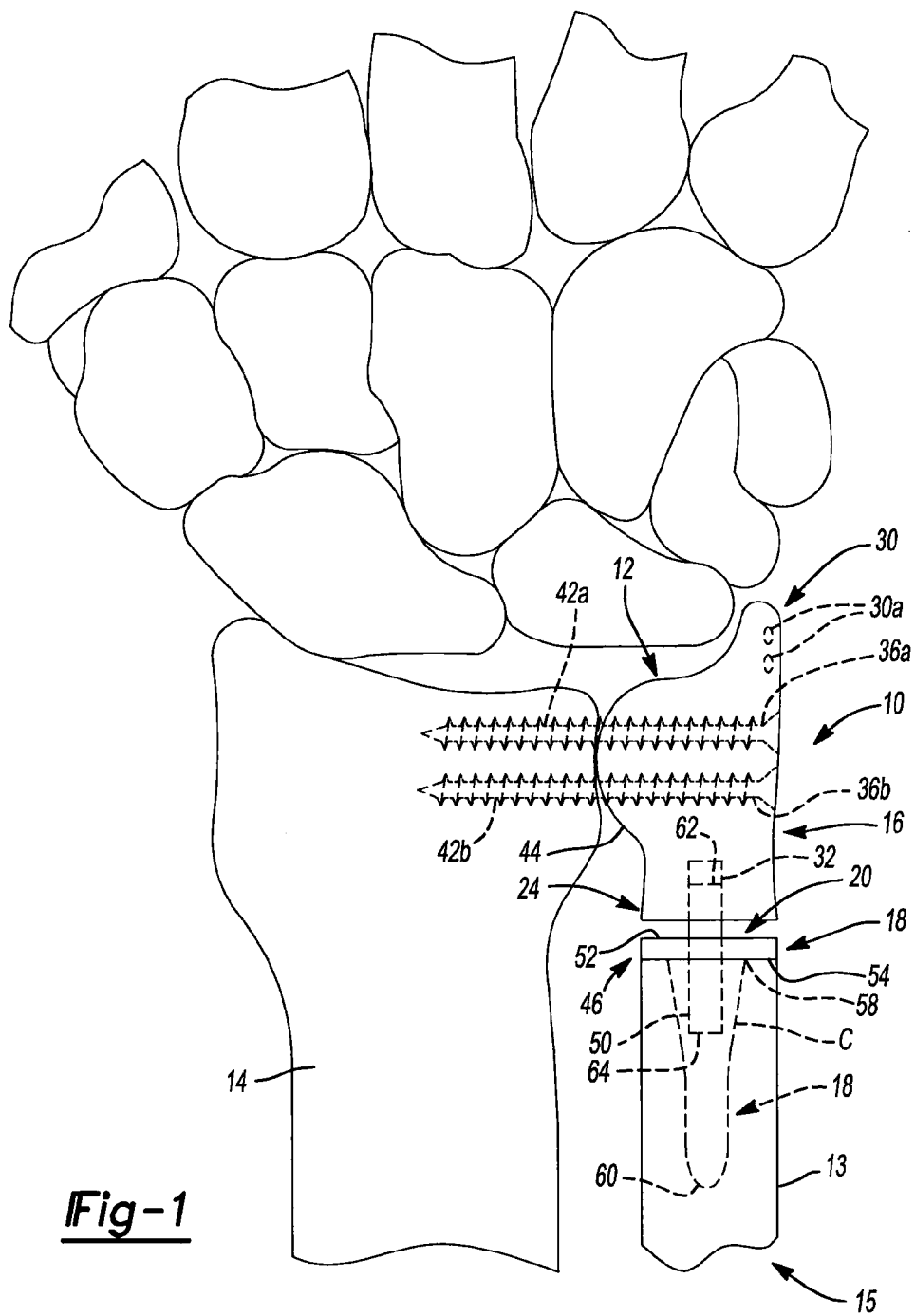
FIG. 1 is an environmental view of an exemplary ulnar head implant according to the present teachings being used to repair a distal radial ulnar joint.

The following description is merely exemplary in nature and is not intended to limit the present teachings, application, or uses. It should be understood that throughout the drawings, corresponding reference numerals indicate like or corresponding parts and features. Although the following description is related generally to an implant for use in an anatomy to restore function to damaged tissue, such as in the case of a distal radial ulnar joint, it will be understood that the teachings of the prosthesis as described and claimed herein can be used in any appropriate surgical procedure. Therefore, it will be understood that the following discussions are not intended to limit the scope of the present teachings and claims herein.

With reference to FIG. 1, an ulnar head implant 10 is shown. The ulnar head implant 10 may be particularly adapted for repairing a distal radial ulnar joint 12. Various aspects of the present teachings, however, may have application for other procedures. In certain applications, as will be discussed further herein, the ulnar head implant 10 can be coupled to a distal end 13 of an ulna 15 to replace a damaged ulnar head. The ulnar head implant 10 can also be coupled to a distal radius 14 to provide stability to the repaired distal radial ulnar joint 12. The ulnar head implant 10 can replicate the natural movement of the ulnar head in the distal radial ulnar joint 12 during supination and pronation of a forearm. With reference to FIGS. 1-4, the ulnar head implant 10 can include a head component or head 16, a stem component or stem 18 and an intermediate component or coupler 20.

Figures 2, 3:
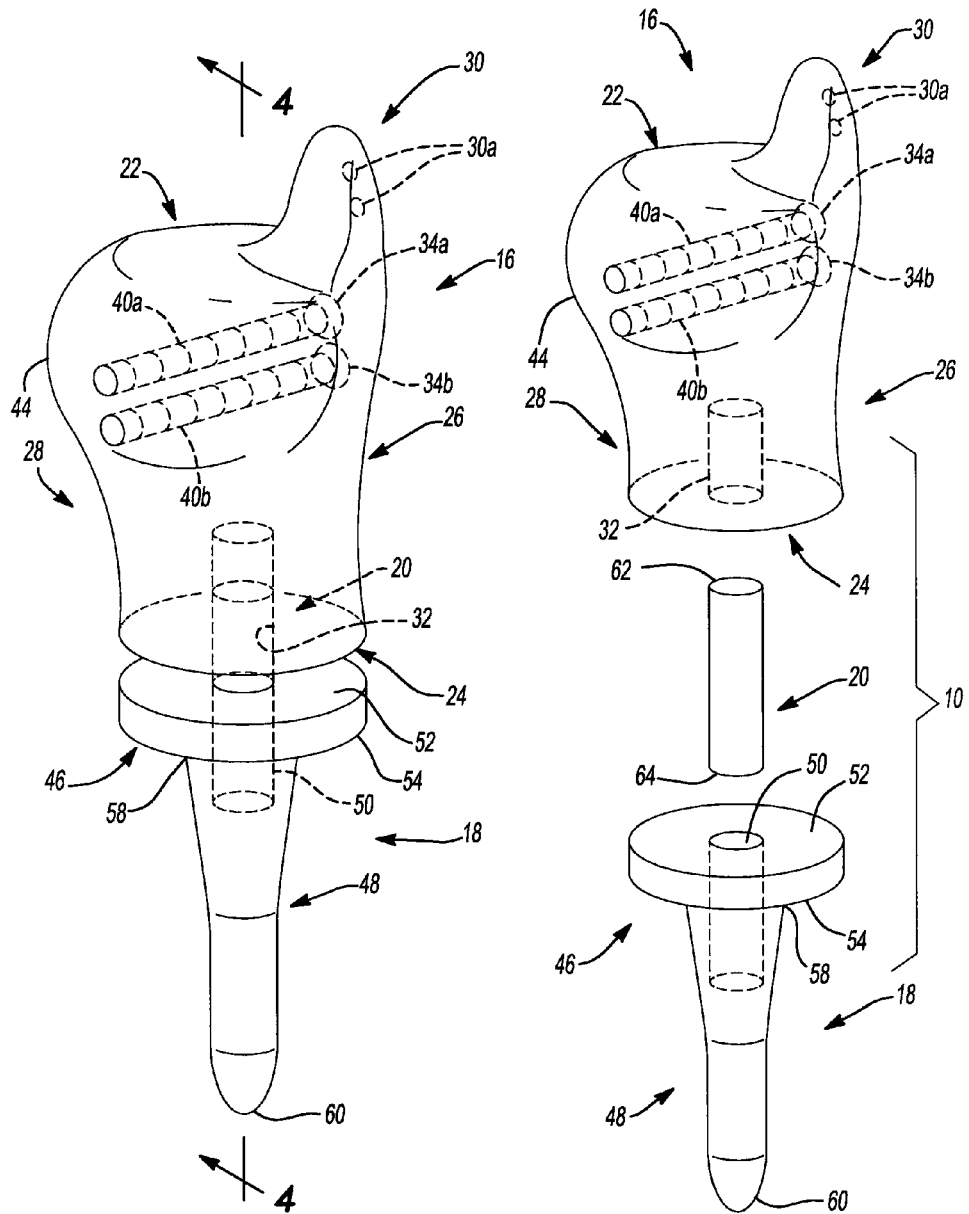
FIG. 2 is a perspective view of the ulnar head implant of FIG. 1.
FIG. 3 is an exploded view of the ulnar head implant of FIG. 1.

With reference to FIG. 2, the head 16 can be coupled to the coupler 20 to enable the head 16 to move relative to the stem 18. The head 16 can be composed of any suitable biocompatible material, such as a biocompatible metal or polymer. For example, the head 16 can be composed of titanium or polyether ether ketone (PEEK) or ultra-high molecular weight polyethylene (UHMWPE). The head 16 can articulate with the distal radius 14. With particular reference to FIGS. 1 and 2, the head 16 can be generally cylindrical, and can include a first or top surface 22, a second or bottom surface 24, a first side 26 and a second side 28.

The top surface 22 can be contoured to mimic the shape of an anatomical ulnar styloid, and can include a projection 30. The projection 30 can be formed to mimic the anatomical ulnar styloid process. If desired, the projection 30 can include one or more apertures 30a, which can receive a suture or other fastening mechanism to assist in attaching one or more ligaments to the head 16, such as the triangular fibrocartilage complex. The bottom surface 24 can be substantially flat or planar, and can define a coupling bore or bore 32. The bore 32 can receive a portion of the coupler 20 to movably couple the head 16 to the stem 18, as will be discussed in greater detail herein.

The first side 26 of the head 16 can be generally opposite the second side 28. The first side 26 can include at least one bore 34. In one example, the first side 26 can include two bores 34a, 34b. The bores 34a, 34b can be defined through the head 16 from the first side 26 to the second side 28, and can extend along an axis transverse to an axis defined by the bore 32. With reference to FIGS. 1 and 2, each of the bores 34a, 34b can receive a fastener or screw 36a, 36b (FIG. 1), which can couple the head 16 to the distal radius 14. The use of the screws 36a, 36b to couple the head 16 to the distal radius 14 can provide stability. The bores 34a, 34b can include internal threads 40a, 40b, if desired, to mate with corresponding threads 42a, 42b on the screws 36a, 36b (FIG. 1). Alternatively, the bores 34a, 34b could have a smooth internal circumference, which could mate with a corresponding smooth exterior surface of a screw 36a, 36b. The second side 28 can include a rounded projection 44. The rounded projection 44 can be shaped to correspond to an anatomical distal ulnar head and can be shaped to articulate with the distal radius 14.

With reference to FIG. 1, the stem 18 can be received within a prepared canal C formed in the distal end 13 of the ulna 15. The stem 18 can be composed of any suitable biocompatible material, such as a biocompatible metal or polymer. For example, the stem 18 can be composed of titanium or PEEK. In one example, the stem 18 can be composed of titanium. In addition, at least a portion of the stem 18 can be coated with a biocompatible material to facilitate bone in-growth to assist in coupling the stem 18 to the anatomy. Exemplary biocompatible materials include a porous metal matrix, such as a porous plasma spray, calcium phosphate, which can include hydroxyapatite, a biologically active substance, such as a bone morphogenic protein, a growth factor, a peptide, antibiotic, REGENEREX® porous titanium construct, etc. Alternatively, or in addition to the coating, cement can be used to couple the stem 18 to the prepared canal C of the ulna 15. With reference to FIG. 2, the stem 18 can include a base 46, a post 48 and a coupling feature or bore 50. It should be noted that although the base 46 and post 48 are illustrated herein as being integrally formed, the base 46 and post 48 could be formed discretely and coupled together through a suitable post processing step, such as welding, etc.

The base 46 can be substantially flat or planar, and can be generally circular in shape. The base 46 can have a first or top surface 52 opposite a second or bottom surface 54. The base 46 can be sized to correspond to the distal end 13 of the ulna 15. The top surface 52 can be positioned adjacent to the bottom surface 24 of the head 16 and can cooperate with the head 16 to enable the head 16 to move relative to the base 46. The bottom surface 54 can be positioned adjacent to the distal end 13 of the ulna 15 and can be coupled to the post 48. The post 48 can be tapered from a first end 58 to a second end 60. The post 48 can be received within the prepared canal C of the distal end 13 of the ulna 15. The bore 50 can be defined through the base 46 and the first end 58 of the post 48. The bore 50 can be formed so as to be generally coaxial with the bore 32 of the head 16. The bore 50 can be substantially cylindrical and can receive a portion of the coupler 20.

With reference to FIG. 3, the coupler 20 can movably couple the head 16 to the stem 18. In one example, the coupler 20 can comprise a substantially cylindrical pin, and can have a substantially smooth exterior. The coupler 20 can be composed of any suitable biocompatible material, such as a biocompatible metal or polymer. For example, the coupler 20 can be composed of titanium, cobalt chromium alloy or PEEK. In one example, the coupler 20 can be composed of PEEK. The coupler 20 can have a first end 62 opposite a second end 64. The first end 62 can be received within the bore 32 of the head 16, and the second end 64 can be received in a portion of the bore 50 formed in the first end 58 of the post 48. Generally, the coupler 20 can move within the bore 32 and the bore 50 and in this example, is not fixed within either the bore 32 or the bore 50. The coupler 20 can have a length L. The length L can be less than a combined length L2 of the bore 32, the bore 50 and a gap formed between the head 16 and the stem 18 when the ulnar head implant 10 is in a rest position as illustrated in FIG. 4. The length L of the coupler 20 can enable the head 16 to piston or move relative to the stem 18. In one example, the head 16 can move relative to the stem 18 in a generally coaxial direction. The movement of the head 16 relative to the stem 18 can reduce loading between the head 16 and the distal radius 14. The generally cylindrical shape of the coupler 20 can enable stem 18 to rotate relative to the head 16. The rotation of the head 16 relative to the stem 18 can enable movement of the forearm through supination and pronation. Generally, the length L can cooperate with the length L2 to constrain the movement of the head 16 relative to the stem 18 by enabling the bottom surface 24 of the head 16 to fully seat against the top surface 52 of the base 46.

With reference to FIG. 1, in order to couple the ulnar head implant 10 to the anatomy, an incision can be made adjacent to the distal end 13 of the ulna 15. Then, a head of the ulna 15 can be resected, and the canal C can be formed in the distal end 13 of the ulna 15. The stem 18 can be inserted into the prepared canal C. If desired, a suitable bone cement can be inserted into the prepared canal C prior to the insertion of the stem 18 to couple the stem 18 to the prepared canal C, and/or the stem 18 including the coating can promote bone in-growth to couple the stem 18 to the prepared canal C. Then, with the coupler 20 inserted into the bore 32 of the head 16, the head 16 can be movably coupled to the stem 18 by inserting the second end 64 of the coupler 20 into the bore 50 of the stem 18. The head 16 can be positioned within the anatomy so that the rounded projection 44 can articulate with the distal radius 14. With the head 16 positioned within the anatomy, the screws 36a, 36b can be threaded through the bores 34a, 34b and into the distal radius 14 to couple the head 16 to the distal radius 14. Then, if desired, a suture can pass through the one or more apertures 30a of the head 16 to couple a ligament, such as the triangular fibrocartilage complex, to the head 16 of the ulnar head implant 10. It should be noted that the use of the screws 36a, 36b to couple the head 16 to the distal radius 14 is optional, as in certain instances where the triangular fibrocartilage complex can be reattached using the suture, screws 36a, 36b may not be needed.

Thus, the ulnar head implant 10 can enable the repair of a damaged distal radial ulnar joint. In this example, the head 16 can move in two degrees of freedom relative to the stem 18. The use of a head 16 that can move in a vertical direction can reduce loading between the head 16 and the distal radius 14. Further, the rotation of the stem 18 relative to the head 16 can enable the ulnar head implant 10 to replicate the natural movement of the distal radial ulnar joint during supination and pronation of the forearm.

In addition, it should be noted that the head 16 and stem 18 can be provided with different sizes to accommodate different patent anatomies. For example, with reference to FIG. 4, the head 16 can have a diameter D1 and a length L3. The head 16 can be provided with different diameters D1 and different lengths L3 to accommodate pediatric patients, adult patients, etc. In one example, the head 16 can be provided with diameters D1 ranging from 12millimeters (mm) to 20 mm and lengths L3 ranging from 10 mm to 18 mm. Heads 16 having different diameters D1 and lengths L3 can be provided as part of a surgical kit, if desired.

The base 46 of the stem 18 can have a diameter D2, and the base 46 can have a length L4. The base 46 can be provided with different diameters D2 and different lengths L4 to accommodate pediatric patients, adult patients, etc. In one example, the base 46 can be provided with diameters D2 ranging from 10 mm to 20 mm and lengths L4 ranging from 2 mm to 20 mm. Stems 18 with bases 46 having different diameters D2 and lengths L4 can be provided as part of a surgical kit, if desired.

Figure 7:
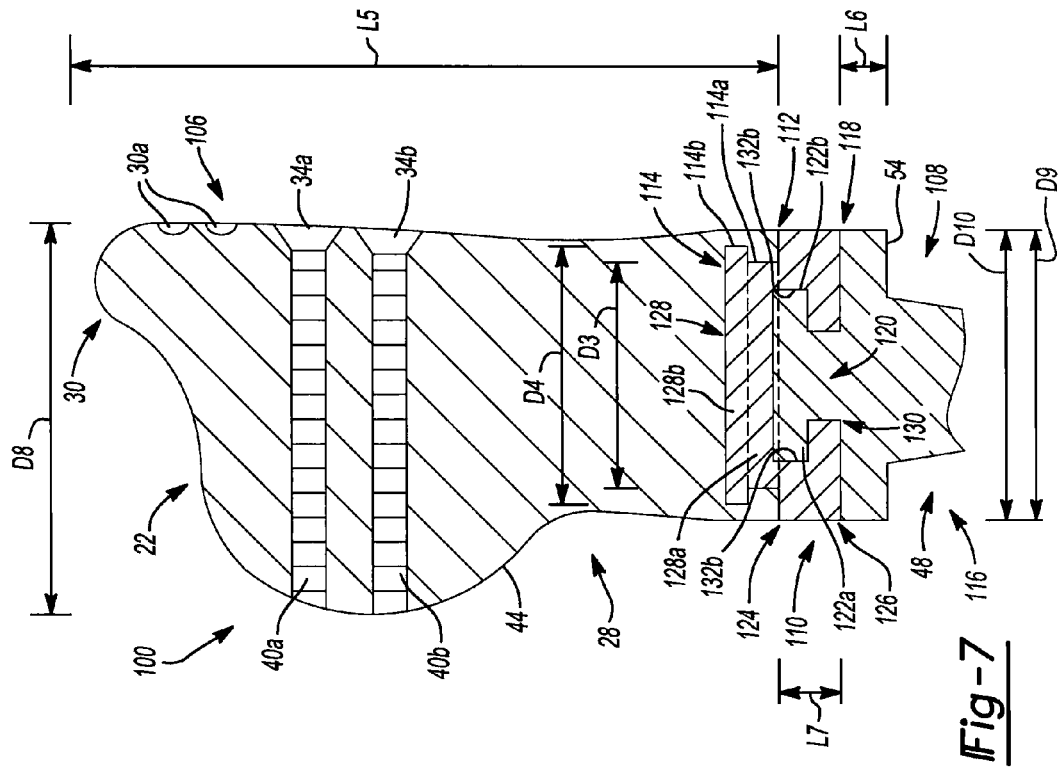
FIG. 7 is a cross-sectional view of the ulnar head implant of FIG. 5, taken along line 7-7 of FIG. 5.
Figure 6:
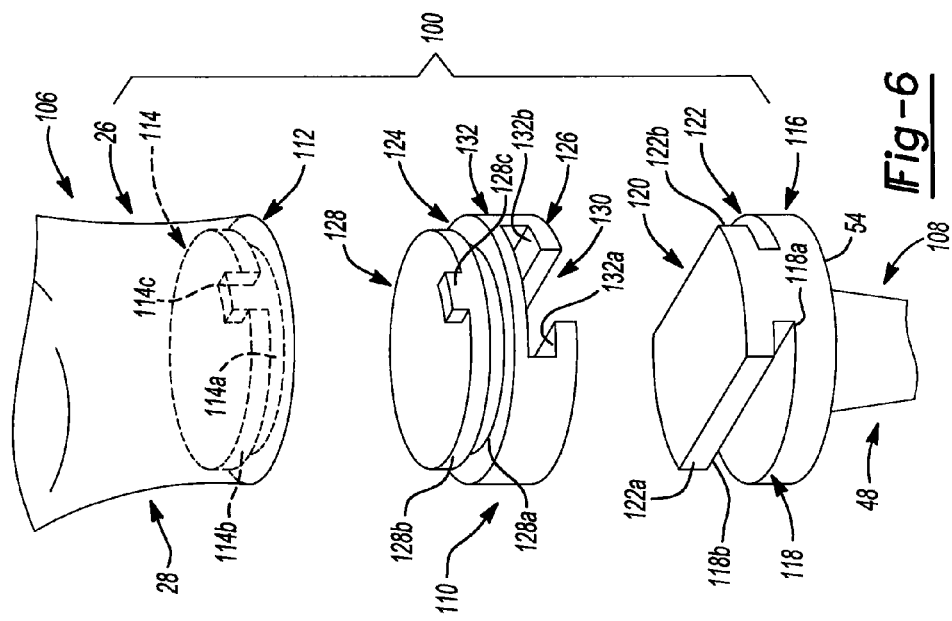
FIG. 6 is an exploded view of the ulnar head implant of FIG. 5.

With reference now to FIGS. 5-7, in one example, an ulnar head implant 100 can be employed to repair a damaged portion of an anatomy. As the ulnar head implant 100 can be similar to the ulnar head implant 10 described with reference to FIGS. 1-4, only the differences between the ulnar head implant 10 and the ulnar head implant 100 will be discussed in great detail herein, and the same reference numerals will be used to denote the same or similar components. With reference to FIG. 5, the ulnar head implant 100 can include a head component or head 106, a stem component or stem 108 and an intermediate component or coupler 110.

The head 106 can be coupled to the coupler 110 to enable the head 106 to move relative to the stem 108. The head 106 can be composed of any suitable biocompatible material, such as a biocompatible metal or polymer. For example, the head 106 can be composed of titanium, UHMWPE or PEEK. The head 106 can articulate with the distal radius 14. With particular reference to FIG. 5, the head 106 can be generally cylindrical, and can include the first or top surface 22, a second or bottom surface 112, the first side 26 and the second side 28.

The bottom surface 112 can be substantially flat or planar, and can define a coupling bore or counterbore 114. The counterbore 114 can receive a portion of the coupler 110 to movably couple the head 106 to the stem 108, as will be discussed in greater detail herein. The counterbore 114 can have a first portion 114a, a second portion 114b and a feature 114c. With reference to FIG. 7, the first portion 114a can have a diameter D3, which can be smaller than a diameter D4 of the second portion 114b. The difference in the diameters D3, D4 can assist in retaining the head 106 on the coupler 110.

The feature 114c can cooperate with a corresponding feature 128c of the coupler 110 to restrict or prevent relative rotation between the head 106 and coupler 110. In one example, the feature 114c can comprise a keyed recess, and the feature 128c can comprise a keyed projection shaped to be received into the keyed recess. It should be noted that the feature 114c and feature 128c can comprise any suitable mating feature that prevents relative rotation between the head 106 and the coupler 110, such as a groove and a tab, etc, which could be positioned on either one of the head 106 and coupler 110. In addition, it should be noted that the use of the feature 114c and feature 128c is merely exemplary as any suitable technique could be employed to prevent the relative rotation, such as the use of a set screw threaded through a bore formed in the head 106 and the coupler 110. Alternatively, the counterbore 114 could be formed in a non-circular shape to mate with a non-circular shaped portion of the coupler 110 to prevent rotation between the head 106 and the coupler 110 once assembled. Further, although the feature 114c is illustrated herein as being formed on the second portion 114b of the head 106, the feature 114c could be formed at any desired location on the head 106. Similarly, although the feature 128c is illustrated herein as being formed on a cylindrical protrusion 128 of the coupler 110, the feature 128c could be formed at any desired location on the head 106.

As discussed with regard to the stem 18 illustrated in FIG. 1, the stem 108 can be received within the prepared canal C formed in the distal end 13 of the ulna 15. With reference to FIG. 5, the stem 108 can be composed of any suitable biocompatible material, such as a biocompatible metal or polymer. For example, the stem 108 can be composed of titanium or PEEK. In one example, the stem 108 can be composed of titanium. In addition, at least a portion of the stem 108 can be coated with a biocompatible material to facilitate bone ingrowth to assist in coupling the stem 108 to the anatomy. Exemplary biocompatible materials include a porous metal matrix, such as a porous plasma spray, calcium phosphate, which can include hydroxyapatite, a biologically active substance, such as a bone morphogenic protein, a growth factor, a peptide, antibiotic, REGENEREX® porous titanium construct, etc. Alternatively, cement can be used to couple the stem 108 within the prepared canal C of the ulna 15. The stem 108 can include a base 116 and the post 48.

The base 116 can be generally circular and can have a first or top surface 118 opposite the second or bottom surface 54. The base 116 can be sized to correspond to the distal end 13 of the ulna 15. The top surface 118 can be coupled to the coupler 110. The top surface 118 can include a coupling feature or a projection 120. With reference to FIG. 6, the projection 120 can have a substantially T-shape, and can define at least one rail 122. Generally, the at least one rail 122 can include two rails 122a, 122b. The rails 122a, 122b can couple the coupler 110 to the stem 108. The projection 120 can extend from a first edge 118a of the top surface 118 to an opposite, second edge 118b of the top surface 118. It should be noted, however, that the projection 120 need not extend from the first edge 118a to the second edge 118b, if desired. Further, the projection 120 need not be T-shaped, but could have any suitable shape to couple the coupler 110 to the stem 108.

With reference to FIGS. 5 and 6, the coupler 110 can couple the head 106 to the stem 108. In one example, the coupler 110 can be substantially cylindrical. The coupler 110 can be composed of any suitable biocompatible material, such as a biocompatible metal or polymer. For example, the coupler 110 can be composed of titanium, cobalt chromium alloy or PEEK. In this example, the coupler 110 can be composed of PEEK. With reference to FIG. 6, the coupler 110 can have a first end 124 and a second end 126. The first end 124 can include the protrusion 128. The protrusion 128 can have a first portion 128a, a second portion 128b and the feature 128c. Generally, the first portion 128a can be sized to be received within the first portion 114a of the counterbore 114 of the head 106, and the second portion 128b can be received within the second portion 114b of the counterbore 114. In one example, the protrusion 128 can be sized to be snap fit into the counterbore 114 of the head 106. It should be noted that although the head 106 and the coupler 110 are described herein being snap fit together, any suitable coupling technique could be used to couple the head 106 to the coupler 110. For example, the head 106 could be molded with the coupler 110. The protrusion 128 of the coupler 110 can be received within the counterbore 114 of the head 106 so that the head 106 can be coupled to the coupler 110. Thus, the first portion 128a can have a diameter, which can be less than the diameter D3 of the first portion 114a of the counterbore 114, and the second portion 128b can have a diameter, which can be less than the diameter D4 of the second portion 114b of the counterbore 114.

With reference to FIG. 6, the second end 126 of the coupler 110 can define a slot 130. The slot 130 can extend through the coupler 110. The slot 130 can be generally T-shaped, and can define at least one guide 132. In one example, the at least one guide 132 can comprise two guides 132a, 132b. As illustrated in FIG. 7, the guides 132a, 132b can receive the rails 122a, 122b of the projection 120 to couple the coupler 110 to the stem 108.

As the surgical insertion of the ulnar head implant 100 can be similar to the surgical insertion of the ulnar head implant 10, the surgical insertion of the ulnar head implant 100 will not be discussed in great detail herein. Briefly, however, with the canal C prepared, with reference to FIG. 5, the stem 108 can be inserted into the prepared canal C. If desired, a suitable bone cement can be inserted into the prepared canal C prior to the insertion of the stem 108 to couple the stem 108 to the prepared canal C, and/or the stem 108 can be coated to promote bone in-growth to couple the stem 108 to the prepared canal C. The protrusion 128 of the coupler 110 can be received in the counterbore 114 of the head 106 to couple the head 106 to the coupler 110. It should be noted that although the coupler 110 is described herein as being coupled to the head intraoperatively, the coupler 110 can be preassembled to the head 106 and packaged together, if desired. Once the coupler 110 is coupled to the head 106, the guides 132a, 132b of the coupler 110 can slidably engage the rails 122a, 122b of the projection 120 to couple the head 106 to the stem 108 via the coupler 110.

The head 106 can be positioned within the anatomy so that the rounded projection 44 can articulate or mate with the distal radius 14. With the head 106 positioned within the anatomy, the screws 36a, 36b can be threaded through the bores 34a, 34b and into the distal radius 14 to couple the head 106 to the distal radius 14, as discussed with regard to the ulnar head implant 10 illustrated in FIG. 1. Then, if desired, a suture can pass through the one or more apertures 30a of the head 106 to couple a ligament, such as the triangular fibrocartilage complex, to the head 106 of the ulnar head implant 100. It should be noted that the use of the screws 36a, 36b to couple the head 106 to the distal radius 14 is optional, as in certain instances where the triangular fibrocartilage complex can be reattached using the suture, screws 36a, 36b may not be needed.

Thus, the ulnar head implant 100 can enable the repair of a damaged distal radial ulnar joint. The use of the coupler 110 and rails 122a, 122b can enable the ulnar head implant 100 to be implanted into the anatomy using a side entry procedure. In addition, it should be noted that the head 106 and stem 108 can be provided with different sizes to accommodate different patent anatomies, as discussed with regard to the head 16 and stem 18 illustrated in FIGS. 1-4. For example, with reference to FIG. 5, the head 106 can have a diameter D8 and a length L5. The head 106 can be provided with different diameters D8 and different lengths L5 to accommodate pediatric patients, adult patients, etc. In one example, the head 106 can be provided with diameters D8 ranging from 12 mm to 20 mm and lengths L5 ranging from 10 mm to 18 mm. Heads 106 having different diameters D8 and lengths L5 can be provided as part of a surgical kit, if desired.

With reference to FIG. 7, the base 116 of the stem 108 can have a diameter D9, and the base 116 can have a length L6. The base 116 can be provided with different diameters D9 and different lengths L6 to accommodate pediatric patients, adult patients, etc. In one example, the base 116 can be provided with diameters D9 ranging from 10 mm to 20 mm and lengths L6 ranging from 2 mm to 20 mm. Stems 108 with bases 116 having different diameters D9 and lengths L6 can be provided as part of a surgical kit, if desired.

In addition, the coupler 110 can have a diameter D10 and a length L7. It should be noted that although the diameter D10 of the coupler 110 is illustrated as be substantially the same as the diameter D9 of the base 116 of the stem 108, the coupler 110 could have a diameter D10 distinct from the diameter D9 of the base 116. The coupler 110 can be provided with different diameters D10 and different lengths L7 to accommodate pediatric patients, adult patients, etc. In one example, the coupler 110 can be provided with diameters D10 ranging from 12 mm to 20 mm and lengths L7 ranging from 8 mm to 20 mm. Couplers 110 having different diameters D10 and lengths L7 can be provided as part of a surgical kit, if desired.

Figure 8:
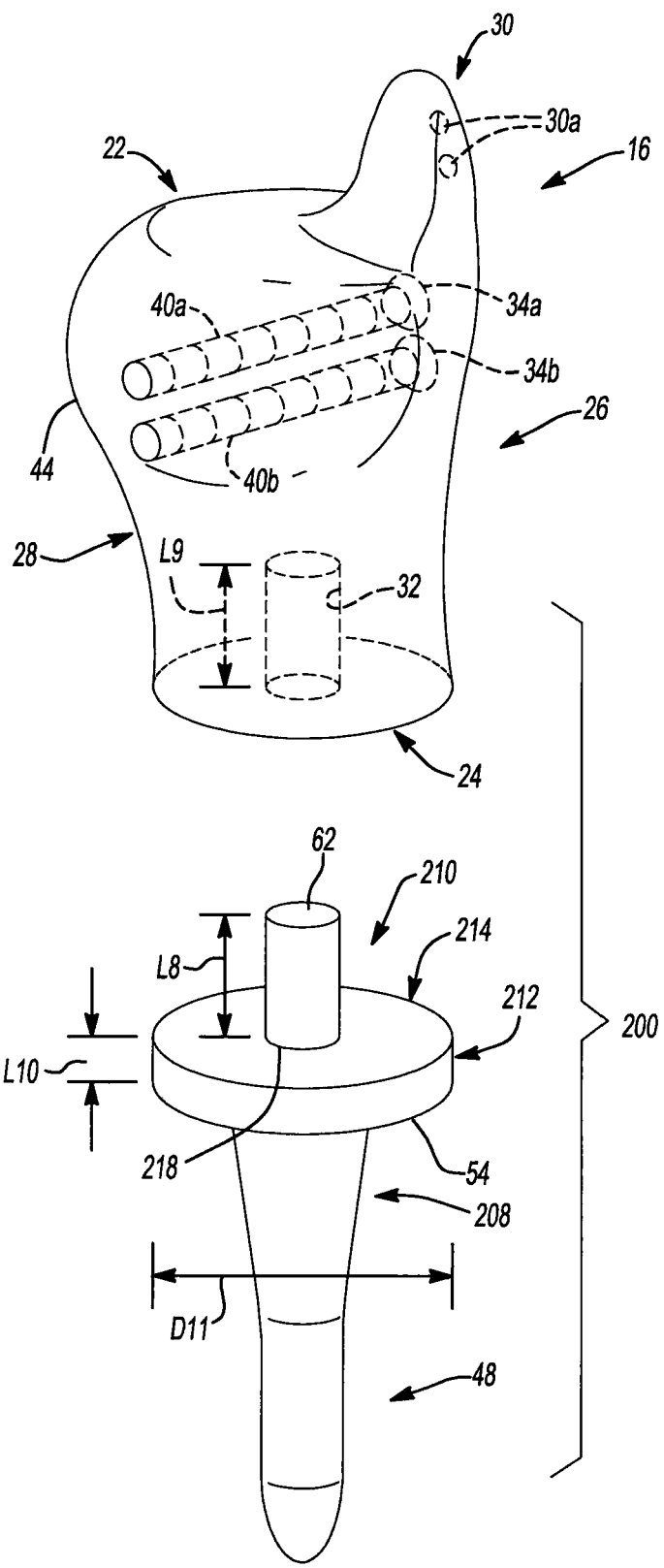
FIG. 8 is an exploded view of another exemplary ulnar head implant according to the present teachings.

With reference now to FIG. 8, in one example, an ulnar head implant 200 can be employed to repair a damaged portion of an anatomy. As the ulnar head implant 200 can be similar to the ulnar head implant 10 described with reference to FIGS. 1-4, only the differences between the ulnar head implant 10 and the ulnar head implant 200 will be discussed in great detail herein, and the same reference numerals will be used to denote the same or similar components. With reference to FIG. 8, the ulnar head implant 200 can include the head component or head 16, a stem component or stem 208 and an intermediate component or coupler 210.

The stem 208 can be received within the prepared canal C formed in the distal end 13 of the ulna 15, as discussed with regard to the stem 18 illustrated in FIG. 1. The stem 208 can be composed of any suitable biocompatible material, such as a biocompatible metal or polymer. For example, the stem 208 can be composed of titanium or PEEK. In one example, the stem 208 can be composed of titanium. In addition, at least a portion of the stem 208 can be coated with a biocompatible material to facilitate bone in-growth to assist in coupling the stem 208 to the anatomy. Exemplary biocompatible materials include a porous metal matrix, such as a porous plasma spray, calcium phosphate, which can include hydroxyapatite, a biologically active substance, such as a bone morphogenic protein, a growth factor, a peptide, antibiotic, REGENEREX® porous titanium construct, etc. Alternatively, cement can be used to couple the stem 208 to the prepared canal C of the ulna. The stem 208 can include a base 212 and the post 48.

The base 212 can have a first or top surface 214 opposite the second or bottom surface 54. The base 212 can be sized to correspond to the distal end 13 of the ulna 15. The top surface 214 can be positioned adjacent to the bottom surface 24 of the head 16 and can cooperate with the head 16 to enable the head 16 to move relative to the base 212. The coupler 210 can be coupled to the top surface 214 of the base 212. In one example, the coupler 210 can be integrally formed with the top surface 214 of the base 212 so as to extend outwardly from the top surface 214. It should be noted that although the coupler 210 is illustrated herein as being integrally formed with the stem 208, the coupler 210 and stem 208 could be discretely formed and coupled together through a suitable post processing step, such as welding, adhesives, etc.

The coupler 210 can movably couple the head 16 to the stem 208. In one example, the coupler 210 can be substantially cylindrical, and can have a substantially smooth exterior. The coupler 210 can be composed of any suitable biocompatible material, such as a biocompatible metal or polymer, which can be the same or a different material than the stem 208. In this example, the coupler 210 can be composed of titanium. The coupler 210 can have the first end 62 opposite a second end 218. The second end 218 can be coupled to the top surface 214 of the base 212. The coupler 210 can have a length L8, which can be less than a length L9 of the bore 32. The shorter length L8 of the coupler 210 can enable the head 16 to piston or move relative to the stem 208. In one example, the head 16 can move relative to the stem 208 in a generally coaxial direction. This movement of the head 16 relative to the stem 208 can reduce loading between the head 16 and the distal radius 14. The generally cylindrical shape of the coupler 210 can enable head 16 to rotate relative to the stem 208. The rotation of the stem 208 relative to the head 16 can enable movement of the forearm through supination and pronation.

As the surgical insertion of the ulnar head implant 100 can be similar to the surgical insertion and insertion of the ulnar head implant 10, the surgical insertion of the ulnar head implant 100 will not be discussed in great detail herein. Briefly, however, with the canal C prepared, the stem 208 can be inserted into the prepared canal C. If desired, a suitable bone cement can be inserted into the prepared canal C prior to the insertion of the stem 208 to couple the stem 208 to the prepared canal C, and/or the stem 208 can be coated to promote bone in-growth to couple the stem 208 to the prepared canal C. Then, the head 16 can be coupled to the stem 208 by inserting the first end 62 of the coupler 210 into the bore 32 of the head 16. The head 16 can be positioned within the anatomy so that the rounded projection 44 can articulate with the distal radius 14. With the head 16 positioned within the anatomy, the screws 36a, 36b can be threaded through the bores 34a, 34b and into the distal radius 14 to couple the head 16 to the distal radius 14, as discussed with regard to the ulnar head implant 10 illustrated in FIG. 1. Then, if desired, a suture can pass through the one or more apertures 30a of the head 16 to couple a ligament, such as the triangular fibrocartilage complex, to the head 16 of the ulnar head implant 200. It should be noted that the use of the screws 36a, 36b to couple the head 16 to the distal radius 14 is optional, as in certain instances where the triangular fibrocartilage complex can be reattached using the suture, screws 36a, 36b may not be needed.

Thus, the ulnar head implant 200 can enable the repair of a damaged distal radial ulnar joint. In this example, the head 16 can move in two degrees of freedom relative to the stem 208. The use of a stem 208 that can move relative to the head 16 can reduce loading between the head 16 and the distal radius 14. Further, the rotation of the stem 208 relative to the head 16 can enable the ulnar head implant 200 to replicate the natural movement of the distal radial ulnar joint during supination and pronation of the forearm.

In addition, as discussed with regard to FIG. 8, the head 16 and stem 208 can be provided with different sizes to accommodate different patent anatomies. For example, the base 212 of the stem 208 can have a diameter D11, and the base 212 can have a length L10. The base 212 can be provided with different diameters D11 and different lengths L10 to accommodate pediatric patients, adult patients, etc. In one example, the base 212 can be provided with diameters D11 ranging from 10 mm to 20 mm and lengths L10 ranging from 2 mm to 20 mm. Stems 208 with bases 212 having different diameters D11 and lengths L10 can be provided as part of a surgical kit, if desired.

Accordingly, the ulnar head implant 10, 100, 200 can be used to repair damaged tissue in the anatomy, such as repairing a distal radial ulnar joint 12. By using a coupler 20, 210, the head 16 can move in at least one degree of freedom relative to the stem 18, 208. This can enable the ulnar head implant 10, 200 to replicate the natural movement of the distal radial ulnar joint 12 during supination and pronation of the forearm. Further, the use of the coupler 20, 210 can reduce loading between the head 16 and the distal radius 14 by allowing the head 16 to move or piston relative to the stem 18, 208. In addition, the use of at least one screw 36 to couple the ulnar head implant 10, 100, 200 to the distal radius 14 can provide additional stability to the distal radial ulnar joint 12. The availability of the head 16, 106, stem 18, 108, 208 and coupler 210 to have various diameters and lengths can also provide a surgeon with a variety of options to suit the needs of various patients.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. An ulnar head implant, comprising:
a prosthetic head component adapted to articulate with a distal radius portion of the anatomy, the prosthetic head component including a first side opposite a second side and defining at least one bore that extends through both the first side and the second side and is configured to align a fastener for coupling the prosthetic head component to a portion of an anatomy, the prosthetic head component further defining a coupling bore through a surface;
a stem component having a base and a post that extends from the base for insertion into a prepared portion of an anatomy, the base including a coupling feature; and
an intermediate component separate from the stem component, the intermediate component receivable within the coupling bore and couplable to the coupling feature to couple the prosthetic head component to the stem component,
wherein the coupling feature of the stem component further comprises a T-shaped projection, and the intermediate component further comprises a T-shaped slot that slidably engages the T-shaped projection to couple the intermediate component to the stem component, further wherein the intermediate component further comprises a protrusion formed opposite the T-shaped slot, which is receivable within the coupling bore to couple the prosthetic head component to the intermediate component.

2. The implant of claim 1, wherein the prosthetic head component has a first surface opposite a second surface, and the coupling bore is defined through the second surface.

3. The implant of claim 2, wherein the first surface includes at least one aperture for receipt of a suture.

4. The implant of claim 1, wherein the coupling bore is defined along a first axis and the at least one bore is defined along a second axis transverse to the first axis.

5. The implant of claim 1, wherein the protrusion includes a feature that cooperates with a feature formed in the coupling bore to prevent relative rotation between the prosthetic head component and the intermediate component once the prosthetic head component is coupled to the intermediate component.

6. An ulnar head implant, comprising:
a prosthetic head component adapted to articulate with a distal radius portion of the anatomy, the prosthetic head component defining at least one bore that extends from a first side to a second, opposite side along a first axis and a counterbore that extends along a second axis transverse to the first axis;

a stem component having a base and a post that extends from the base for insertion into a prepared portion of an anatomy; and an intermediate component separate from the stem component, the intermediate component receivable within the counterbore of the prosthetic head component to enable the prosthetic head component to move relative to the stem component about at least two degrees of freedom, wherein the intermediate component is coupled to the base of the stem component and the intermediate component has a length less than a length of the counterbore of the prosthetic head component to enable the prosthetic head component to move coaxially relative to the stem component.

7. The implant of claim 6, wherein the prosthetic head component has a first surface opposite a second surface, and the counterbore is defined through the second surface.

8. The implant of claim 7, wherein the first surface includes at least one aperture for receipt of a suture.

9. The implant of claim 6, wherein the at least one bore defined by the prosthetic head component further comprises two bores formed through the prosthetic head component, each for receipt of a fastener for coupling the prosthetic head component to a portion of an anatomy.

10. The implant of claim 6, wherein the stem component further comprises a bore and the intermediate component further comprises a substantially cylindrical pin receivable within the coupling bore and the bore of the stem component to movably couple the prosthetic head component to the stem component.

11. A method of using an ulnar head implant, comprising:

coupling a stem component to a first portion of an anatomy;

coupling an intermediate component to a counterbore of a prosthetic head component, the intermediate component being a separate component from the stem component;

coupling the intermediate component to the stem component so that that the prosthetic head component is movable relative to the stem component about at least one degree of freedom, wherein the intermediate component has a length less than a length of the counterbore of the prosthetic head component to enable the prosthetic head component to move coaxially relative to the stem component; and inserting at least one fastener through a bore defined in the prosthetic head component to secure the prosthetic head component to a distal radius portion of the anatomy.

12. The method of claim 11, further comprising:

coupling the intermediate component to the stem component so that the prosthetic head component moves coaxially relative to the stem component.

13. The method of claim 12, further comprising:

coupling the intermediate component to the stem component so that the stem component rotates relative to the prosthetic head component.

* * * * *